United States Patent [19]

Balsley et al.

[11] 4,320,130

[45] Mar. 16, 1982

[54] BAIT COMPOSITIONS FOR THE CONTROL OF INSECTS PREPARED FROM PREGEL CORN AND A TOXICANT

[75] Inventors: Richard B. Balsley, Lebanon; Abdel H. Marei, Mercerville, both of N.J.

[73] Assignee: American Cyanamid Co., Stamford, Conn.

[21] Appl. No.: 125,595

[22] Filed: Feb. 28, 1980

[51] Int. Cl.³ .................. A01N 25/00; A01N 43/54
[52] U.S. Cl. ........................ 424/251; 424/84
[58] Field of Search ............... 424/84, 251

[56] References Cited

U.S. PATENT DOCUMENTS

| | | | |
|---|---|---|---|
| 4,087,528 | 5/1978 | Perua et al. | 424/251 |
| 4,152,422 | 5/1979 | Ohinata et al. | 424/84 |
| 4,163,102 | 7/1979 | Lovell | 424/251 |
| 4,213,988 | 7/1980 | Lovell | 424/251 |

FOREIGN PATENT DOCUMENTS

| | | | |
|---|---|---|---|
| 848945 | 8/1970 | Canada | 424/225 |
| 44-320 | 9/1969 | Japan | 424/84 |
| 47-23198 | 6/1972 | Japan | 424/84 |
| 111917 | 7/1962 | Pakistan | 424/219 |
| 333218 | 8/1930 | United Kingdom | 424/84 |

*Primary Examiner*—Allen J. Robinson
*Attorney, Agent, or Firm*—H. G. Jackson

[57] ABSTRACT

There is provided a pesticidal bait composition useful for the control of insects, such as fire ants. There is also provided a method of preparation of said baits, whereby pregel defatted corn grits are blended with a solution of a toxicant in a mixture of an edible oil, such as soyabean oil, and a higher fatty acid, such as oleic or stearic acid.

5 Claims, No Drawings

BAIT COMPOSITIONS FOR THE CONTROL OF INSECTS PREPARED FROM PREGEL CORN AND A TOXICANT

The present invention relates to an insecticidal composition useful for the control of insects. More particularly, it relates to insecticidal bait compositions which include pregel defatted corn grits and 5,5-dimethyl-2(1H)-pyrimidinone-{3-[4-(trifluoromethyl)phenyl]-1-{2-[4-(trifluoromethyl)phenyl]ethenyl}-2-propenylidene}hydrazone as a toxicant dissolved in a mixture of a higher fatty acid and an edible oil, wherein said toxicant solution is admixed with and absorbed on the above pregel corn grits.

In general, the insecticidal bait composition of the present invention is prepared in a straightforward manner. An insecticide which is active as a stomach poison, such as the insecticide hereinabove named, can be graphically illustrated by formula:

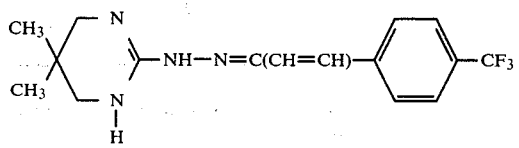

The latter is disclosed in U.S. Pat. No. 4,163,102 and its method of use is disclosed in both U.S. Pat. No. 4,087,525, as well as U.S. Pat. No. 4,213,988, all of which are incorporated herein by reference. The insecticide is dissolved at a rate of from about 1% to about 10% and, preferably, from 2.5% to 5.0% of the formulation in a mixture of oleic acid used in amounts ranging from 2% to about 20% and, preferably, 5.0% to 10.0% of the formulation, and of refined soybean oil used in amounts sufficient to total said formulation to 100%. The thus-obtained pesticidal solution is then admixed with and absorbed on pregel defatted corn grits to yield bait compositions comprising 70% to 80% of defatted pregel corn grits, 0.2% to 3.0% of a compound of formula (I), 0.4% to 6.0% of oleic acid and 11.0% to 29.4% of refined soybean oil, all percentages being by weight.

Overall bait compositions for the control of fire ants comprise 70–80% of pregel defatted corn grits and 20–30% of a toxicant solution containing 2.5–4.4% of a formula (I) toxicant, resulting in a bait which contains 0.50% or 0.88% of toxicant, respectively, all percentages being by weight. The thus-prepared baits are quite stable in contrast to similar preparations wherein pregel degermed corn grits, puffed corn balls or corncob grits are substituted for pregel defatted corn grits, respectively.

The above referred-to carriers can be further characterized as follows:

a Pregel defatted corn grits are 10/30 mesh size brownish yellow solids, obtained by steam extruding wet corn meal, which contains some of the germ portion of the ground corn kernels, and which has previously been treated with a solvent to remove any oil present in said meal.

b Pregel degermed corn grits are 10/30 mesh size brownish yellow solids, obtained by steam extruding wet corn meal which contains almost no germ.

c Puffed corn balls are 10/30 mesh size yellow solid balls obtained by extruding yellow corn flour, followed by drying.

d Corncob grits are 10/30 mesh size light brown chips obtained by grinding the woody portion of corncobs after removal of the pith and draff.

In addition, data, pertaining to the grinding and of separating corn kernels into their respective components, can be found in U.S. Pat. No. 3,287,138, issued Nov. 22, 1966, and is incorporated herein by reference.

Baits of the above described composition are effective against insects with chewing mouth parts (Orthopterous insects such as cockroaches, grasshoppers, crickets and Isopterous insects, such as termites). They are effective for the control of fire ants, such as the southern fire ant, *Solenopsis xyloni*, the black imported fire ant, *Solenopsis richteri* and the red imported fire ant, *Solenopsis invicta*. They are also effective for the control of ants, such as the big-headed ant, *Pheidole megacephala*, and the Argentine ant, *Iridomyrmax humilis*, that are dominant pests in pineapple and sugarcane fields, and for the control of many species of ants that are classified under the general category of household ants. Ants are serious economic and public health pests. Serious problems created by fire ants are stinging of humans and livestock, feeding on plants, particularly on seedlings and on germinating seeds, damage to farm machinery that strike ant mounds, loss of crops and refusal of workers to enter infested fields to cultivate and harvest crops. Ants invade houses, crawl over food, carry bits of food to their nests and also cause damage by establishing their nests in the woodwork of houses and other wooden buildings.

Control of these pests can be achieved with treated baits that are distributed in or adjacent to the infested area, such as pasture, park dwellings or other locations in which ant control is desired, and made available to worker ants. The workers carry the treated bait to the colony where it is consumed by the queens and the young ants, leading to their destruction.

In practice, generally about 1.25 g/ha to 75.0 g/ha, and preferably 2.5 g/ha to 37.5 g/ha of formula (I) compound is effective for fire ant control and/or for crop protection from ants and about 0.0625% to 4% by weight, and preferably 0.125% to 2.0% by weight of said compound is effective for the control of house ants and/or other insects that are controlled by bait.

Baits can be prepared with or without an attractant, such as lecitin. The composition is then distributed in the area of the colony or infestation. Use of these baits has particular advantage, since such method of distribution poses little or no hazard to non-target organism that may frequent the infested area.

The invention is further illustrated by the examples set fourth below. These examples are provided only by way of illustration and are not intended to be limiting.

EXAMPLE 1

Preparation of a solution containing 2.5% by weight of toxicant

A mixture of tetrahydro-5,5-dimethyl-2(1H)-pyrimidinone-{3-[4-(trifluoromethyl)phenyl]-1-{2-[4-(trifluoromethyl)phenyl]ethenyl}-2-propenylidine}hydrazone (90–95% pure; 27.33 kg) and oleic acid (50 kg) is stirred and heated at 50° C. until a clear solution forms. Soybean oil (once refined) is added to the above solution in amounts sufficient to adjust the total weight of the solution to 1000 kg.

The storage stability of the above solution is determined by storing samples of same in amber glass bottles at room temperature (RT), at 37° C. and 45° C., respectively. The samples are analyzed after one, two and three months storage. The data obtained are summarized in Table I below.

TABLE I

| | Percent by weight of toxicant found in the stored samples, as indicated | | |
|---|---|---|---|
| Time | RT | 37° C. | 45° C. |
| initial | 2.58 | — | — |
| 1 month | 2.44 | 2.27 | 2.30 |
| 2 months | — | — | 2.48 |
| 3 months | 2.73 | 2.63 | 2.46 |

By the above procedure, but using only 13.66 kg of the above toxicant and 25.0 kg of oleic acid, a 1000 kg batch of solution is prepared, containing 1.25% by weight of toxicant.

EXAMPLE 2

Preparation of a granular bait containing 0.75%, by weight, of toxicant

Pregel defatted corn grits (700 kg) are agitated in a blender and sprayed with 300 kg of a solution prepared by the method of Example 1, and containing 2.5% by weight of tetrahydro-5,5-dimethyl-2(1H)-pyrimidinone-{3-[4-(trifluoromethyl)phenyl]-1-{2-[4-(trifluoromethyl)phenyl]ethenyl}-2-propenylidene}hydrazone. After all of the liquid has been added, blending is continued for about 5 minutes or until all of the liquid is absorbed.

The storage stability of the above granular bait is determined by storing representative samples of same at room temperature (RT), 37° C. and at 45° C., respectively. The samples are analyzed after one, two and three months storage. The data obtained are summarized in Table II below.

TABLE II

| | Percent by weight of toxicant found in the stored samples, as indicated | | |
|---|---|---|---|
| Time | RT | 37° C. | 45° C. |
| initial | 0.71 | — | — |
| 1 month | 0.73 | 0.72 | 0.71 |
| 2 months | — | — | 0.64 |
| 3 months | 0.72 | 0.67 | 0.52 |

By the above method, but substituting pregel degermed corn grits for pregel defatted corn grits, a granular bait is prepared containing 0.75% by weight of the above toxicant.

The storage stability of the above granular bait is determined by storing representative samples of same at room temperature (RT), 37° C. and at 45° C., respectively. The samples are analyzed after one, two and three months storage. The data obtained are summarized in Table III below.

TABLE III

| | Percent by weight of toxicant found in the stored samples, as indicated | | |
|---|---|---|---|
| Time | RT | 37° C. | 45° C. |
| initial | 0.69 | — | — |
| 1 month | 0.68 | 0.66 | 0.55 |
| 2 months | — | — | 0.21 |

TABLE III-continued

| | Percent by weight of toxicant found in the stored samples, as indicated | | |
|---|---|---|---|
| Time | RT | 37° C. | 45° C. |
| 3 months | 0.66 | 0.29 | 0.018 |

By the above method, but substituting puffed corn for pregel defatted corn grits, a granular bait is prepared containing 0.75% by weight of the above toxicant.

The storage stability of the above granular bait is determined by storing representative samples of same at room temperature (RT), 37° C. and at 45° C., respectively. The samples are analyzed after one, two and three months storage. The data obtained are summarized in Table IV below.

TABLE IV

| | Percent by weight of toxicant, found in the stored samples, as indicated | | |
|---|---|---|---|
| Time | RT | 37° C. | 45° C. |
| initial | 0.71 | — | — |
| 1 month | 0.74 | 0.72 | 0.52 |
| 2 months | — | — | <0.04 |
| 3 months | 0.66 | none found | — |

By the above method, but substituting corncob grits for pregel defatted corn grits, and increasing the amount of carrier used, a granular bait is prepared containing 0.385% by weight of toxicant.

The storage stability of the above granular bait is determined by storing representative samples of same at room temperature (RT), 37° C. and at 45° C., respectively. The samples are analyzed after one, two and three months storage. The data obtained are summarized in Table V below.

TABLE V

| | Percent by weight of toxicant found in the stored samples, as indicated | | |
|---|---|---|---|
| Time | RT | 37° C. | 45° C. |
| initial | .33 | — | — |
| 1 month | .34 | .33 | .33 |
| 2 months | — | — | .21 |
| 3 months | .34 | .32 | .12 |

It can be concluded from a consideration of Tables II to V that bait compositions prepared with defatted pregel corn grits are more stable than compositions using different carriers.

EXAMPLE 3

Evaluation of the efficacy of baits prepared by the method of the invention for the control of fire ants The test area selected is reforested land, infested with imported fire ants (*Solenopsis invicta* Buren). The test plots are approximately 40.5 ha (100 acres) in size. Within each test plot there are 13 to 22 subplots, approximately 0.2 ha (0.5 acre) in size, randomly distributed over said plot. The number of pretreatment counts[1] of active mounds of imported fire ants in the subplots varies from 246 to 265.

The granular baits prepared by the methods of Examples 1 and 2 are broadcast from an airplane flying at an altitude of approximately 9 meters (30 feet) with a speed of approximately 193 km/h (120 mph), resulting in a swath of approximately 18.3 meters (60 feet) wide treated land.

Eight weeks posttreatment the percent fire ant control is determined. The data obtained are summarized in Table VI below.

(1) The pre- and posttreatment counts of active mounds are determined by using a system which taken into account the size of the fire ant mound.

Accordingly, the mounds are ranked in the following categories:

1. Mound with <100 ants and without worker brood.
2. Mound with 100–1000 ants and without worker brood.
3. Mound with 1000–10,000 ants and without worker brood.
4. Mound with 10,000–50,000 ants and without worker brood.
5. Mound with >50,000 ants and without worker brood.
6. Mound with <100 ants and with worker brood.
7. Mound with 100–1000 ants and with worker brood.
8. Mound with 1000–10,000 ants and with worker brood.
9. Mound with 10,000–50,000 ants and with worker brood.
10. Mound with >50,000 ants and with worker brood.

To arrive at the above referred—to "count" per subplot, the number of mounds within each subplot are counted according to their rank and then multiplied by the rank (category) number. The thus obtained numbers, when totaled per subplot, yield the corresponding "count" of active mounds found.

EXAMPLE 4

Evaluation of the efficacy of baits of the invention for the control of fire ants The test area selected is reforested land, infested with imported fire ants (*Solenopsis invicta* Buren). The test plots are approximately 4 ha (10 acres) in size. Within each test plot there are 2 to 4 subplots, approximately 0.20 ha (0.5 acre) in size, randomly distributed over said plot. The number of pretreatment counts[1] of active mounds of imported fire ants in the subplots varies from 98 to 124.

The granular baits prepared by the methods of Examples 1 and 2 are broadcast from a helicopter flying at an altitude of approximately 23 meters (75 feed) with a speed of approximately 121 km/h (75 mph), resulting in a swath of approximately 24.4 meters (80 feet) wide treated land.

Eight weeks posttreatment the percent fire ant control is determined. The data obtained are summarized in Table VII below.

(1) The "counts" are determined as described in Example 3.

TABLE VII

Evaluation of the efficiency of baits of various compositions for the control of imported fire ants

| Carrier | % Concentration of Toxicant in Oil | % Concentration of Toxicant in Bait | Bait; rate of application kg/ha | Toxicant; rate of application g/ha | No. of active mounds, pre treatment | % reduction in active mounds after 8 weeks |
|---|---|---|---|---|---|---|
| Puffed Corn | 2.5 | 0.7 | 1.39 | 9.6 | 124 | 84 |
| Pregel defatted corn grits | 2.5 | 0.7 | 0.81 | 5.7 | 111 | 82 |
|  |  |  | 0.81 | 5.7 | 98 | 95 |
|  |  |  | 1.51 | 10.6 | 109 | 85 |
|  |  |  | 2.80 | 19.5 | 120 | 100 |
| Pregel degermed corn grits | 2.5 | 0.7 | 0.95 | 6.7 | 105 | 58 |
|  |  |  | 0.95 | 6.7 | 128 | 39 |
|  |  |  | 1.74 | 12.1 | 111 | 92 |
|  |  |  | 2.37 | 16.6 | 123 | 97 |
| Corncob grits | 2.5 | 0.33 | 2.80 | 9.1 | 117 | 70 |
|  |  |  | 2.82 | 9.4 | 99 | 76 |

We claim:

1. A stable, solid, free flowing, particulated insecticidal bait composition comprising: from 70% to 80% of pregel defatted corn grits, and from 20% to 30% of a solution wherein said solution comprises from 1% to 10% of tetrahydro-5,5-dimethyl-2-(1H)-pyrimidinone-{3-[4-(trifluoromethyl)phenyl]-1-{2-[4-(trifluoromethyl)phenyl]ethenyl}-2-propenylidene}hydrazone, in admixture with about 2% to 20% of oleic acid and soybean oil in amounts sufficient to total said solution to 100%, all percentages being by weight.

TABLE VI

Evaluation of the efficiency of baits of various composition for the control of imported fire ants

| Carrier | % Concentration of Toxicant in Oil | % Concentration of Toxicant in Bait | Bait; rate of application kg/ha | Toxicant; rate of application g/ha | No. of active mounds, pre treatment | % reduction in active mounds after 8 weeks |
|---|---|---|---|---|---|---|
| Puffed Corn | 2.5 | 0.7 | 2.69 | 18.8 | 265 | 62 |
| Pregel defatted corn grits | 2.5 | 0.7 | 0.86 | 5.9 | 255 | 79 |
|  |  |  | 0.86 | 5.9 | 246 | 89 |
|  |  |  | 1.36 | 9.4 | 246 | 98 |
|  |  |  | 1.83 | 12.6 | 255 | 88 |
| Pregel degermed corn grits | 2.5 | 0.7 | 0.87 | 6.2 | 261 | 67 |
|  |  |  | 0.87 | 6.2 | 253 | 79 |
|  |  |  | 1.75 | 12.4 | 248 | 94 |
|  |  |  | 2.05 | 14.3 | 259 | 70 |

2. The composition according to claim 1 comprising in combination from 70% to 80% of pregel defatted corn grits, from 0.2% to 3.0% of said hydrazone, from 0.4% to 6.0% of oleic acid, and 17.3% to 29.4% of soybean oil, all percentages being by weight.

3. The composition according to claim 1 comprising in combination: 70% of pregel defatted corn grits, 0.375% of said hydrazone of claim 1, 0.75% of oleic acid and 28.875% of soybean oil, all percentages being by weight.

4. The composition according to claim 1 comprising in combination: 80% of pregel defatted corn grits, 0.88% of said hydrazone of claim 1, 1.76% of oleic acid and 17.46% of soybean oil, all percentages being by weight.

5. The composition according to claim 1 comprising: 80% by weight of composition of pregel defatted corn grits, 0.55% by weight of said hydrazone of claim 1, 1.1% of composition of oleic acid and 18.35% of composition of soybean oil, all percentages being by weight.

* * * * *